(12) United States Patent
Fonte

(10) Patent No.: US 9,039,766 B1
(45) Date of Patent: May 26, 2015

(54) WAVE SPRING FOR A SPINAL IMPLANT

(75) Inventor: Matthew Fonte, Charlestown, MA (US)

(73) Assignee: MX Orthopedics, Corp., Cambridge, MA (US)

( * ) Notice: Subject to any disclaimer, the term of this patent is extended or adjusted under 35 U.S.C. 154(b) by 0 days.

(21) Appl. No.: 13/536,109

(22) Filed: Jun. 28, 2012

Related U.S. Application Data

(60) Provisional application No. 61/503,076, filed on Jun. 30, 2011.

(51) Int. Cl.
*A61F 2/44* (2006.01)
*A61F 2/30* (2006.01)

(52) U.S. Cl.
CPC ......... *A61F 2/442* (2013.01); *A61F 2002/4435* (2013.01); *A61F 2002/444* (2013.01); *A61F 2002/30566* (2013.01); *A61F 2002/30571* (2013.01); *A61F 2002/30573* (2013.01); *A61F 2/44* (2013.01)

(58) Field of Classification Search
CPC ........... A61F 2/442; A61F 2002/30563; A61F 2002/30565; A61F 2002/4435; A61F 2002/444; A61F 2002/30566; A61F 2002/30571; A61F 2002/30573
USPC ..................... 606/246–249; 623/17.11–17.16
See application file for complete search history.

(56) References Cited

U.S. PATENT DOCUMENTS

| | | | |
|---|---|---|---|
| 5,885,074 A * | 3/1999 | Hanson | 433/13 |
| 6,440,169 B1 | 8/2002 | Elberg et al. | |
| 6,966,910 B2 | 11/2005 | Ritland | |
| 7,632,292 B2 | 12/2009 | Sengupta et al. | |
| 7,794,476 B2 | 9/2010 | Wisnewski | |
| 2005/0043796 A1 | 2/2005 | Grant et al. | |
| 2006/0079898 A1 * | 4/2006 | Ainsworth et al. | 606/61 |
| 2008/0065074 A1 | 3/2008 | Yeung et al. | |
| 2009/0138085 A1 * | 5/2009 | Simonson | 623/17.13 |
| 2009/0192617 A1 * | 7/2009 | Arramon et al. | 623/17.16 |
| 2009/0222097 A1 * | 9/2009 | Liu et al. | 623/17.16 |
| 2009/0292363 A1 * | 11/2009 | Goldfarb et al. | 623/17.16 |
| 2010/0211106 A1 | 8/2010 | Bowden et al. | |
| 2010/0249848 A1 | 9/2010 | Wisnewski | |

* cited by examiner

*Primary Examiner* — Ellen C. Hammond
*Assistant Examiner* — Christina Negrellirodrigue
(74) *Attorney, Agent, or Firm* — Sunstein Kann Murphy & Timbers LLP

(57) ABSTRACT

A spinal implant includes a wave spring configured to surround a nucleus. The spring may be formed from a shape memory material. The implant may further include an artificial nucleus configured to simulate a disc nucleus.

20 Claims, 13 Drawing Sheets

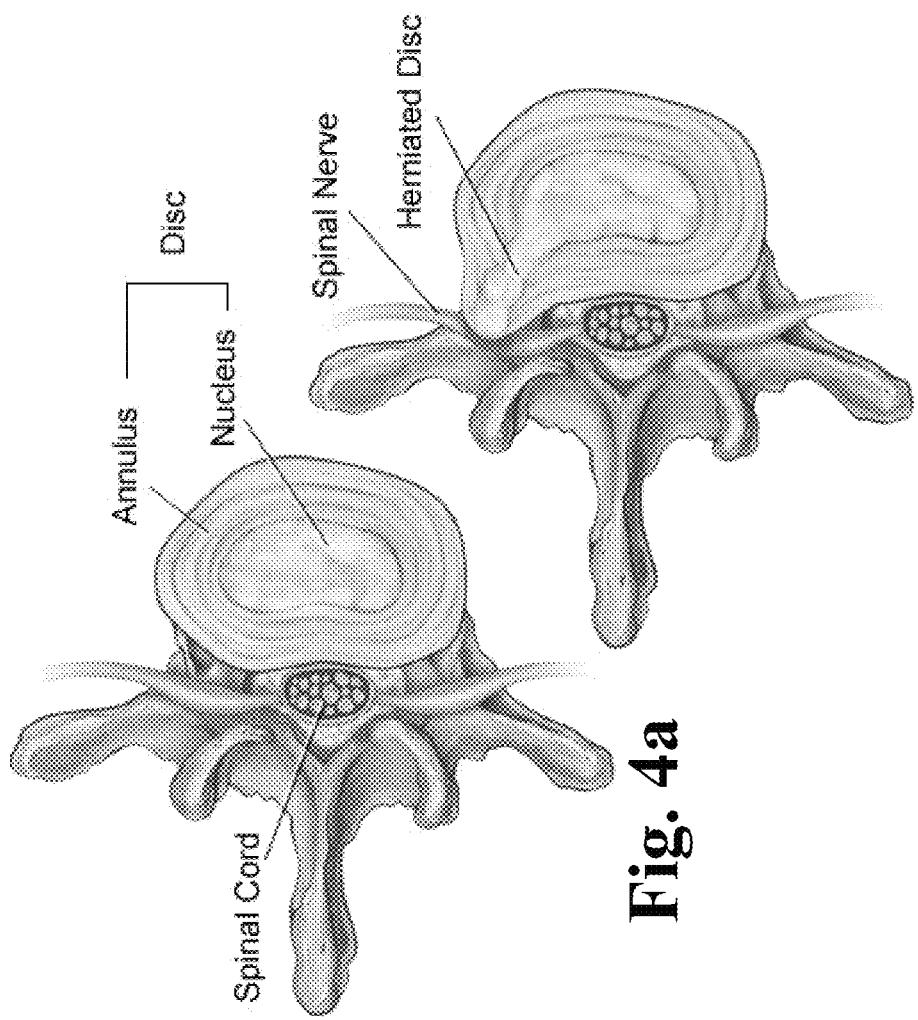

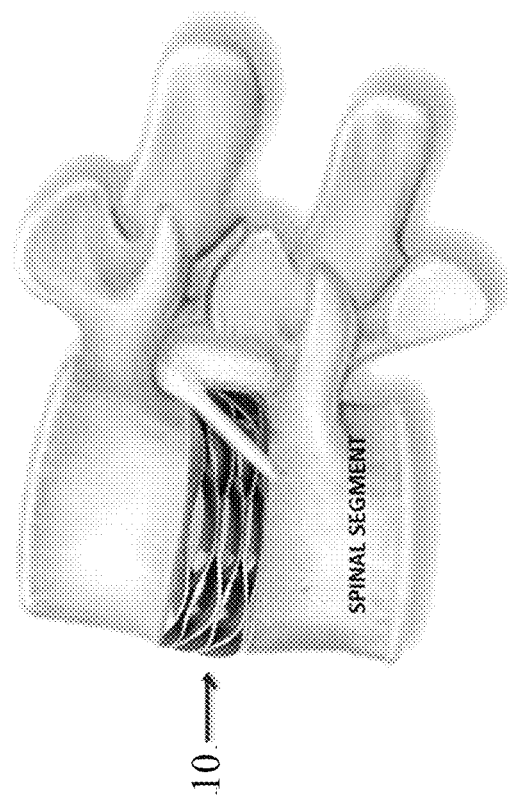
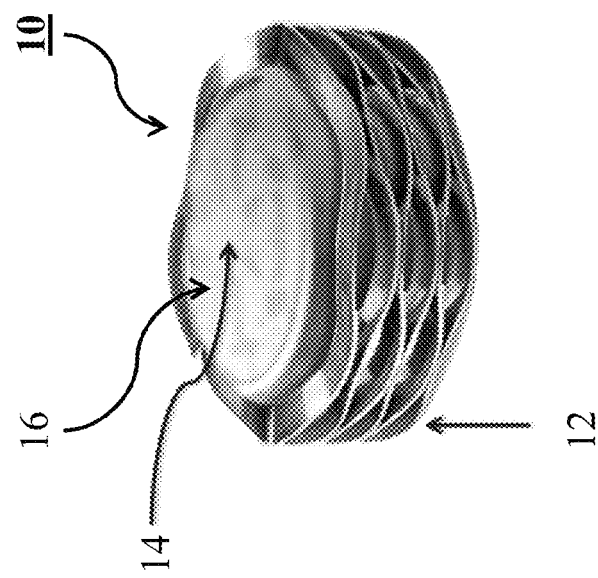
Fig. 8
Fig. 7

WAVE SPRING FOR A SPINAL IMPLANT

CROSS-REFERENCE TO RELATED APPLICATIONS

This patent application claims priority to U.S. Provisional Patent Application No. 61/503,076 filed Jun. 30, 2011, entitled SHAPE MEMORY MATERIAL SPINAL IMPLANT, the disclosure of which is incorporated by reference herein in its entirety.

TECHNICAL FIELD

The present invention relates to medical devices, and more particularly to spinal implants.

BACKGROUND ART

The vertebral column, also called the backbone, is made up of 33 vertebrae that are separated by spongy discs and classified into five areas: (1) the cervical vertebrae which consists of seven bony parts in the neck; (2) the thoracic vertebrae which consists of 12 bony parts in the back area; (3) the lumbar vertebrae which consists of five bony segments in the lower back area; (4) the sacrum which consists of five sacral bones fused into one; and (5) the coccyx which consists of four coccygeal bones fused together into one. The five areas of the spine are shown in FIG. 1.

Lumbar disc disease occurs in the lumbar area of the spine. The lumbar area of the spine (and other areas of the spine) is made up of two parts:

vertebral bodies—the parts that are made of bone.

intervertebral discs—also known as simply as discs. The discs are located between the bony parts of the spine and act as "shock absorbers" for the spine.

FIG. 2 shows an example of an intervertebral disc located between two vertebral bodies. The vertebral bodies are numbered from 1 to 5 in the lumbar area and the discs that are located between two of the vertebral bodies are numbered accordingly (e.g., L2-3, (or the disc located between vertebral bodies 2 and 3)).

Each intervertebral disc is composed of two parts: (1) the annulus fibrosis—a tough outer ring of fibrous tissue, and (2) nucleus pulposus—located inside the annulus fibrosis. The nucleus is composed of a more gelatinous or soft material.

As humans age, the intervertebral disc may become dehydrated and compressed. This condition leads to the deterioration of the tough outer ring. FIG. 3 shows a healthy disc and a degenerated disc. As the tough outer ring degenerates, in some cases, the nucleus is pushed against the ring and eventually bulges out of the ring. This is considered a "bulging disc". As the disc continues to degenerate, and with continued stress on the spine, the inner nucleus pulposus may actually rupture out from the annulus. This is considered a ruptured, or herniated, disc. FIG. 4a shows an example of healthy disc, and FIG. 4b shows an example of a herniated disc. The fragments of disc material can then press on the nerve roots that are located just behind the disc space. This can cause pain, weakness, numbness, or changes in sensation. Most disc herniations happen in the lower lumbar area, particularly in the L4-5 and L5-S1 areas. FIG. 5 shows a herniated disc, while FIG. 6 shows an example of a healthy disc. Note the uneven distribution of forces on the herniated disc.

Lumbar disc disease is due to a change in the structure of the normal disc. Most times, disc disease is the result of aging and the degeneration that occurs within the disc. Occasionally, severe trauma can cause a normal disc to herniate and trauma may cause an already herniated disc to worsen.

Spinal fusion is a surgery that fuses vertebrae together. Typically, two vertebrae are permanently coupled so that there is no longer any movement between them. In some cases, the surgeon will use a graft (such as bone) to hold (or fuse) the bones together permanently. There are several different ways of fusing vertebrae together. In one example, strips of bone graft material may be placed over the back part of the spine to fuse two vertebrae together. In another example, the bone graft material is placed between the vertebrae. In yet another example, a special cage is placed between the vertebrae and the cage is filled with bone graft material. In further examples, the vertebrae are fused together using screws, plates, and/or cages.

There are many disadvantages associated with spinal fusion. Spinal fusion is designed to eliminate the normal motion of one or more lumbar segments in the spine. Accordingly, the spinal column above and below the fusion area is more likely to be stressed when the spine does move. Thus, persistent stress can cause future problems in un-fused areas of the spine.

Disc nucleus replacement is a procedure that replaces the soft jelly center of the natural disc (or a portion thereof) with a prosthetic disk nucleus (PDN) such as an artificial gel sac. The gel sac alleviates pain and further damage by acting as a shock absorber that prevents the spine from applying pressure to the nerves. Another potential benefit of the gel space is that it allows more movement of the spine, and therefore prevents disk degeneration below and above the site of surgery. As a result, the gel sac allows the cartilage surrounding the nucleus to heal and the patient can resume normal activity. Disc nucleus replacement surgery can be performed using a minimally invasive laparoscopic procedure, which is performed through tiny cuts using miniature tools and viewing devices.

One example of an in-situ curable polyurethane nucleus replacement device is the DASCOR™ Disc Arthroplasty device. The DASCOR™ device is made by mixing two-parts of liquid polymer while delivering it through a catheter to an expandable polyurethane balloon that is placed in the disc space. The polymer cures in a matter of minutes, changing state from a liquid to a firm, but pliable solid device. After 15 minutes, the delivery catheter is removed, leaving the final implant device. The balloon catheter has a low profile and can be inserted into the disc space through a small annulotomy (e.g., 5.5 mm). The mixed liquid polymer is delivered to the balloon under controlled pressure, causing the balloon to expand to contour and fill the entire disc space left by the nucleotomy procedure.

The use of the in-situ curable device provides for implantation of a large volume device through a small annulotomy, thus making migration of the solidified device unlikely. Additionally, the system has the versatility of creating an implant of whatever size that is created by the nucleotomy.

Also, the device can be used in combination with other components such as endplates that are affixed to the vertebrae. In particular, the deployment of a large and pliable device located between the endplates and that contours to the endplates can help balance associated load transfer between the annulus and the artificial nucleus while minimizing endplate disruption.

Another related advantage of the in-situ curable device is its ability to generate distraction forces inside the nucleotomy space. Therefore, the implantation of the device not only offers the ability to fill any given space left by nucleotomy, but also the potential to distract and restore a collapsed intervertebral disc.

A disadvantage associated with the in-situ curable device is that the polymer might not be robust enough over time to support the compressive loads of the spine.

Total disc replacement is another example of a spinal surgery. In some cases, the entire disc is beyond repair and a complete disc replacement is necessary. In such an instance, total disc replacement can be performed instead of spinal fusion surgery. Nonetheless, total disc replacement has not yet been shown to be superior to spinal fusion. Total disc replacement involves replacing the disc with an artificial disc. Some artificial discs (such as ProDisc, Link, SB Charite) consist of two metal plates and a soft core.

The SBCharité III is an example of an artificial disc used to replace an entire disc. The SBCharité III is composed of two endplates of high quality cobalt chromium alloy. The endplates are coated with titanium and a hydroxyapatite porous coating to enhance bone fixation (osteointegration). The endplates are fixed to each vertebrae using anchoring teeth along the edges of the plates. The natural movement of the disc is made possible with a dense polyethylene sliding core that is placed between the endplates. In this manner, the core acts as a spacer to maintain a natural distance between the two vertebrae and also more naturally supports the spinal column.

Unlike spinal fusion, disc replacement technologies (such as the DASCOR™ and the SBCharité III) do not require grafts and provide for a more natural movement of the spine so that further injuries to the spine are diminished. To this end, disc replacement technologies attempt to restore and maintain normal physiological motion. This is accomplished by (1) restoring and maintaining a natural intervertebral separation height, (2) restoring and maintaining a natural lordosis, (3) restoring and maintaining a natural instantaneous axis of rotation; (4) correcting abnormal motion; (5) reducing or eliminating pain in the spine, and (6) improving functional ability of the patient. If these goals are achieved, the segments of the spine adjacent to the artificial disc will be free of abnormal loads and motions. Accordingly, there would be a deceleration or elimination of stress applied to spine segments adjacent the artificial disc.

There are some disadvantageous associated with current disc replacement technologies. Artificial discs that use polymer materials tend to degenerate because polymer strength diminishes over time, especially under loads, a phenomenon known as creep. As the polymer materials degenerate, the core between the endplates of the artificial disc will wear thin, changing the intervertebral distance and causing wear debris to undesirably migrate into the spinal area. The patient may react to this debris with an inflammatory response that can cause pain, implant loosening, and further implant failure.

The artificial disc device itself may also be a source of complications. The device can shift out of its normal position and even dislocate. If the device migrates out of position, it can cause injury to the nearby tissues. A second surgery may be needed to align or replace the device. Similar to other types of joint replacements, the artificial disc device may fail over time as its components degenerate. An artificial disc device is estimated to last 15 to 20 years. Once the device fails, it is removed and typically replaced with spinal fusion surgery.

Subsidence is another possible problem of artificial disc devices. Subsidence happens when the disc device sinks down into the vertebral body or is pushed up into the vertebral body. Subsidence can result in a loss of the normal disc height, which, in turn, could result in the compression of nerves and adverse neurological symptoms.

SUMMARY OF THE EMBODIMENTS

Illustrative embodiments of the present invention are directed to a spinal implant that includes a wave spring configured to surround a nucleus. Other illustrative embodiments are directed to a method of forming a spinal implant that includes forming a spring having a shape of a wave spring, and configuring the spring to surrounding a nucleus. Other illustrative embodiments are directed to a method of implanting a spinal implant that includes inserting a wave spring into an intervertebral space, and introducing a nucleus material into an interior area of the spring. The nucleus material is configured to simulate a natural disc nucleus.

In various illustrative embodiments, the spinal implant may further include an artificial nucleus configured to simulate a disc nucleus, and the spring surrounds the artificial nucleus. The artificial nucleus may be made from a polymer material, a hydro-gel material, and/or a wave spring. The spring may be wedge shaped. The spring may be made of a shape memory material, stainless steel, titanium, titanium alloy, and/or a cobalt chrome alloy. The shape memory material may be Nitinol and/or a Titanium-Niobium alloy. The spring may be formed with one or more flat wires and/or rectangular wires.

BRIEF DESCRIPTION OF THE DRAWINGS

The foregoing features of embodiments will be more readily understood by reference to the following detailed description, taken with reference to the accompanying drawings, in which:

FIGS. 4a and 4b show examples of a healthy disc and a herniated disc, respectively;

FIG. 7 shows a spinal implant with a spring wave and a nucleus located within the spring, in accordance with one embodiment of the present invention;

FIG. 8 shows a spinal implant implanted within the space between the intervertabral space in accordance with one embodiment of the present invention;

DETAILED DESCRIPTION OF SPECIFIC EMBODIMENTS

Illustrative embodiments of the present invention are directed to a spinal implant 10 that includes a spring 12, such as a wave spring, configured for insertion into an intervertebral space, for example, as shown in FIGS. 7 and 8. In various illustrative embodiments, the spring 12 has a controlled stiffness, offers many degrees of motion, provides for the shock absorption of the vertebrae, acts as a spacer between the vertebrae, may support an inner artificial nucleus pulpous and/or helps to prevent stress shielding of the vertebrae. In further exemplary embodiments, the spring 12 is loaded and tuned to have the same modulus as bone and may be formed from a shape memory material.

In various illustrative embodiments, the spinal implant 10 may further include an artificial nucleus 14 which is designed to simulate the function of the natural disc nucleus. The spring 12 is configured to surround the natural disc nucleus or the artificial nucleus 14, which is preferably formed of a compressible material such as a compressible polymer and/or hydro-gel material. Additionally, or alternatively, the artificial nucleus 14 can be made from a spring, for example a wave spring. The spring can be designed to have mechanical properties similar to the native, natural disc nucleus.

The spring 12 forms an interior area 16 that is configured to hold the artificial nucleus 14. FIG. 7 shows a spinal implant 10 with a wave spring 12 and a nucleus 14 located within the spring 12, in accordance with one embodiment of the present invention. In such an embodiment, the spring is used as a fiber annulus and is intended to facilitate a controlled range of motion of the spine. In various illustrative embodiments, the spring is "tuned" as explained above to match the modulus of the vertebral bone. In additional or alternative embodiments, the spring 12 will help to restore the distance between the vertebrae. In yet further embodiments, the spring 12 will support the compressive and torsional loads on an artificial polymer nucleus 14, while also being elastic so that stress shielding is minimized.

In further illustrative embodiments, the spring is compressed to facilitate a minimally invasive implantation. FIG. 8 shows a wave spring implanted within the space between the vertebrae in accordance with one embodiment of the present invention. In various embodiments, the spring is compressed to provide for the insertion of the artificial polymer nucleus. In other illustrative embodiments, the artificial nucleus 14 is injected into the core of the spring 12 after it is implanted.

Figure 1:
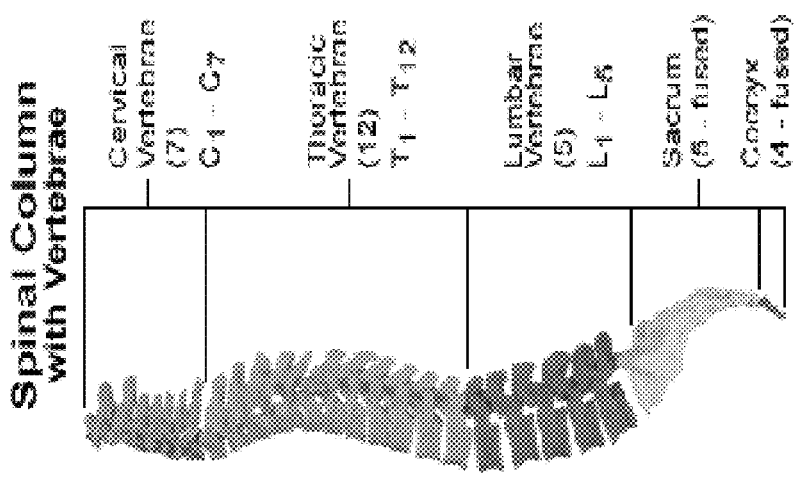
FIG. 1 shows the five areas of the spine.
Figure 2:
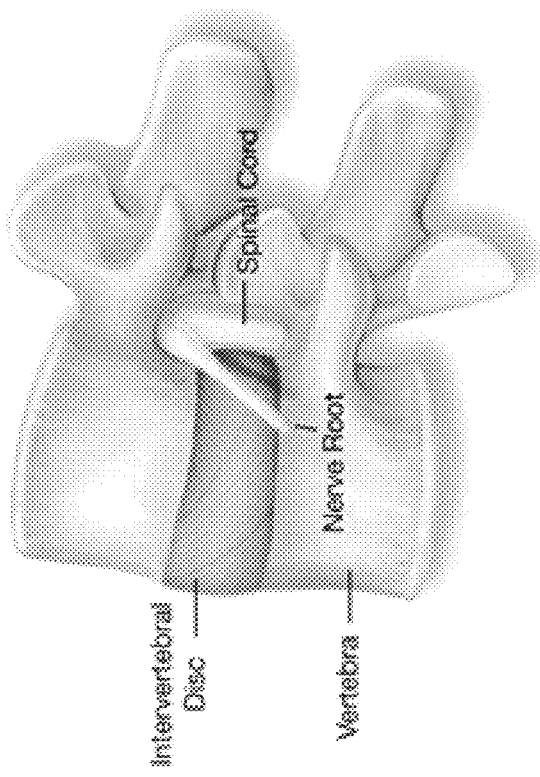
FIG. 2 shows an example of an intervertebral disc located between two vertebral bodies.
Figure 3:
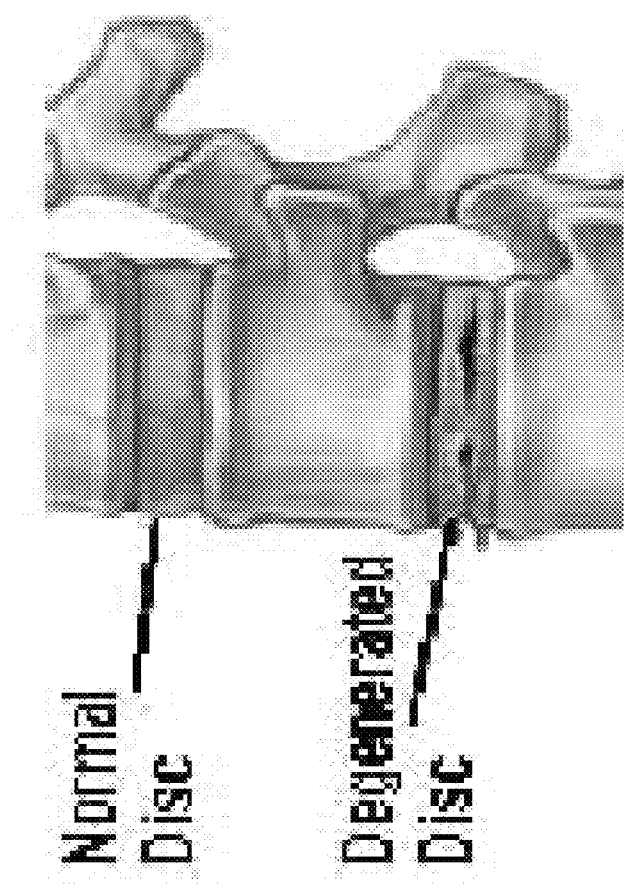
FIG. 3 shows a healthy disc and a degenerated disc.
Figure 6:
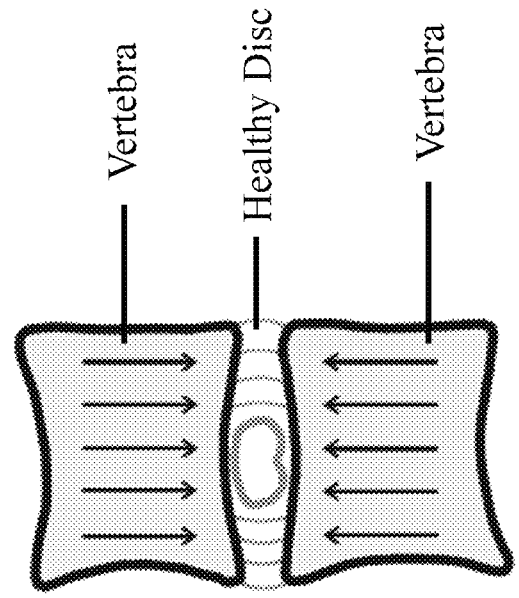
FIG. 6 shows another example of a healthy disc with the distribution of forces on the disc.
Figure 5:
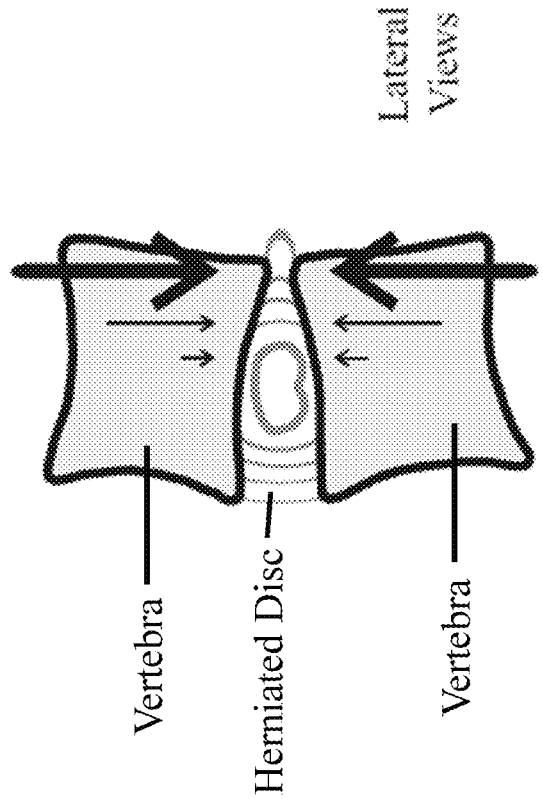
FIG. 5 shows another example of a herniated disc with the uneven distribution of forces on the disc.
Figure 9:
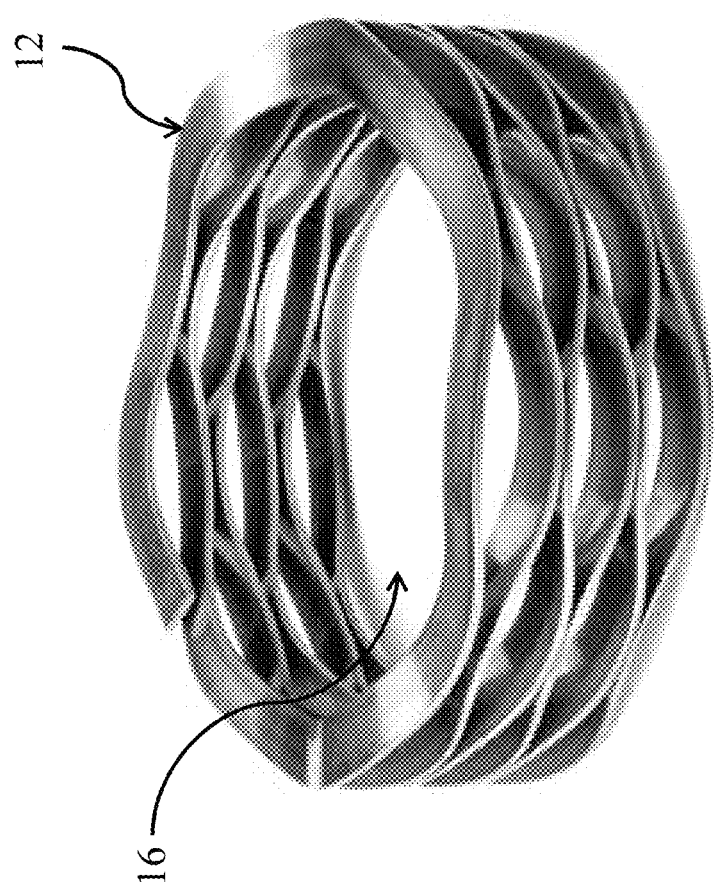
FIG. 9 shows a wave spring in accordance with one embodiment of the present invention.
Figures 10A, 10B:
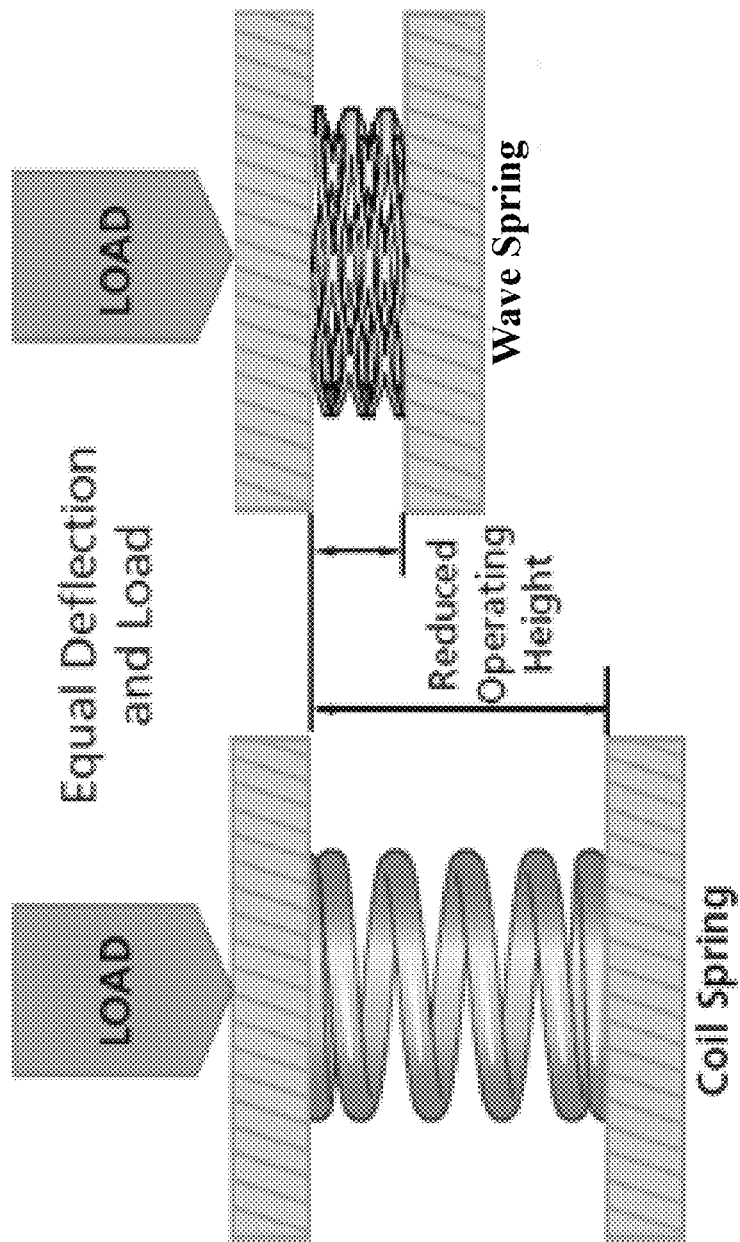
FIGS. 10a and 10b show a conventional coil spring and a wave spring, respectively, in accordance with one embodiment of the present invention.

In illustrative embodiments of the present invention, the spring 12 can be one of a compression spring, a stacked Belleville washer springs, and/or wave spring. FIG. 9 shows a wave spring in accordance with one embodiment of the present invention. A wave spring is a coiled flat wire, or multiple flat wires, with waves. Wave springs are superior to coil springs in certain applications because they provide lower operating heights while supporting the same loads. As shown in FIGS. 10a and 10b, wave springs are typically stiffer than conventional coil springs and therefore have a reduced operating height as compared to coil springs. Thus, wave springs require less space between and within the vertebrae. The wave spring not only provides for space savings, but also for smaller assemblies that use less materials and thus lower production costs.

Wave springs are a type of compression spring made from an elongated flat strip of material which is circularly coiled and has a sinusoidal wavepath. Springs are defined by a spring constant which specifies the amount the spring will deflect when a known load is applied to it. The spring constant of a wave spring is determined by modulus of elasticity of the material, the radial wall thickness, the mean diameter, the number of waves per turn, the initial height of the spring, and the thickness of the material. Varying these parameters allows a user to tune a spring for a particular application, such as to match the modulus of an intervertebral disc. Additionally, the spring can patient specific ie: different dimensions and spring constant for positioning at different levels of the spinal column, and tailored for patients of different height and weight.

Wave springs can be manufactured using a single turn, crest-to-crest, or nested design. Single turn springs are manufactured from a single rotation of the sinusoidal wavepath material. Crest-to-crest springs are pre-stacked in series, with the peaks of one layer aligning with the valleys in the adjacent layer. This stacking decreases the spring rate by a factor relative to the number of turns. Nested springs are pre-stacked in parallel, with the peaks and valleys of the sinusoidal path aligning on top of each other. This stacking increases the spring rate by a factor relative to the number of turns. The above mentioned spring types can additionally be manufactured with flat shims on the top and bottom surfaces of the spring, to more uniformly distribute the load from the spring to the adjacent surfaces.

Wave springs allow for the preservation of anatomical motion. As the spine moves, adjacent vertebrae will eccentrically load the wave spring and regions of the spring will experience tension, while the remaining portion will be in a state of compression. Owing to the sinusoidal coiling, wave springs permit all six degrees of freedom: compression, lateral shear, sagittal shear, flexion/extension, lateral bending, and torsion. Additionally, because the spring can be made from a strip of material instead of a wire, wave springs resist shear loads more strongly than conventional wound springs. This is important for maintaining the stability of the spine, especially during early healing.

Wave springs can act as load bearing devices by compensating for accumulated tolerances in assemblies and providing end-play take up. In other words, wave springs exert a force, or "preload" on an assembly made to the lower end of a tolerance and thereby insure there is coupling between the components of the assembly. On the other hand, wave springs also "give" when the components of an assembly are made to the high end of the tolerance. The "preload" and "give" properties of the wave spring allow for the spring to support vertebral loads more naturally while the load conditions on the spine vary.

The spring 12 of the spinal implant 10 can be made from any biocompatible materials, e.g., shape memory materials, titanium or titanium alloys, stainless steel, and other similar materials. In one illustrative embodiment, the springs 12 are made from shape memory metal materials such as a Nickel-Titanium alloy (Nitinol) or a Titanium-Niobium alloy. In various illustrative embodiments, the shape memory material offers more "spring" as compared to other alloys because many shape memory materials are superelastic. Nitinol alloys are known for their superelasticity and thermal shape memory. The term "shape memory effect" is used herein to describe the ability of shape memory materials to recover to a predetermined shape upon heating (after having been plastically deformed). The term "superelasticity" refers to the ability of the materials to be deformed elastically. For example, Nitinol alloys can be 10 times more elastic as compared to stainless steels used in the medical field.

Figure 11:
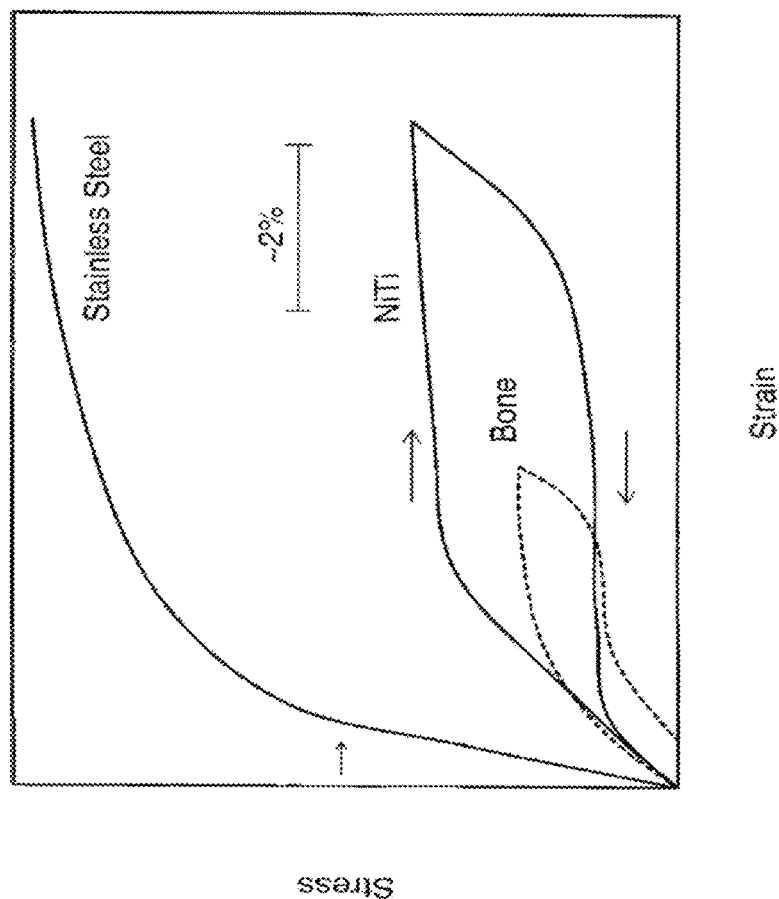
FIG. 11 shows the stress-strain curve of Nitinol (NiTi), bone, and stainless steel in accordance with one embodiment of the present invention.

Furthermore, certain shape memory materials, such as Nitinol alloys, follow a non-linear path characterized by a pronounced hysteresis. Nitinol alloys follow the same stress-strain hysteresis curve as bone, thereby making it a very compatible material with bone. This relationship is illustrated in FIG. 11, which shows the stress-strain curve of Nitinol, bone, and stainless steel.

Illustrative embodiments of the spinal implant 10 formed with a shape memory spring 12 include various other advantageous. For example, the superelasticity of shape memory materials allows the spring to be inserted into the body with a small compressed profile, making implantation a minimally invasive procedure. Once inside the body, the devices can be released from a constraining means and then can unfold or expand to a much larger size. A spinal spring formed from shape memory materials can be compressed, inserted into the space between the vertebrae, and then allowed to expand into place between the vertebrae.

Another illustrative advantage of a spinal implant 10 formed with a shape memory spring 12 is the shape memory characteristics of shape memory materials. For example, a shape memory material spring with a transition temperature (austenitic start temperature) of 30° C. can be compressed below its transition temperature. The spring will stay compressed until the temperature is raised above 30° C. It will then expand to its preset shape. In one illustrative embodiment of the present invention, the spring device is kept below its transition temperature while being inserted into the body. Once inserted into the space between the vertebrae, the spring temperature exceeds its transition temperature due to body heat and the spring expands into its preset shape.

In various embodiments of the present invention, the spring 12 is constrained while being inserted into the body in order to prevent premature deployment. Shape memory material springs could be built with transition temperatures of 40° C. or higher. Such devices would need to be heated after delivery into the body in order to initiate expansion.

Yet another illustrative advantage of using a shape memory material spring in a spinal implant is that its loading and unloading curves are substantially flat over large strains. This loading curve allows exemplary embodiments of the spring to apply a constant force. Various illustrative embodiments of the spinal spring offer a constant stress under varying loading and unloading conditions (e.g., when a person is walking or laying down, respectively). Illustrative embodiments of the shape memory material spring will apply a constant force against the vertebrae.

A further illustrative advantage of using a shape memory material spring in a spinal implant is its dynamic interference. The dynamic interference is the long-range nature of shape memory material stresses. For example, unlike an expandable stainless steel spring, self-expanding shape memory material springs expand to their preset shape without recoil. Self-expandable steel springs typically must be over-expanded to achieve a certain diameter as a result of elastic spring-back. This spring-back, or loosening, is called acute recoil and is a highly undesirable feature.

Figure 12:
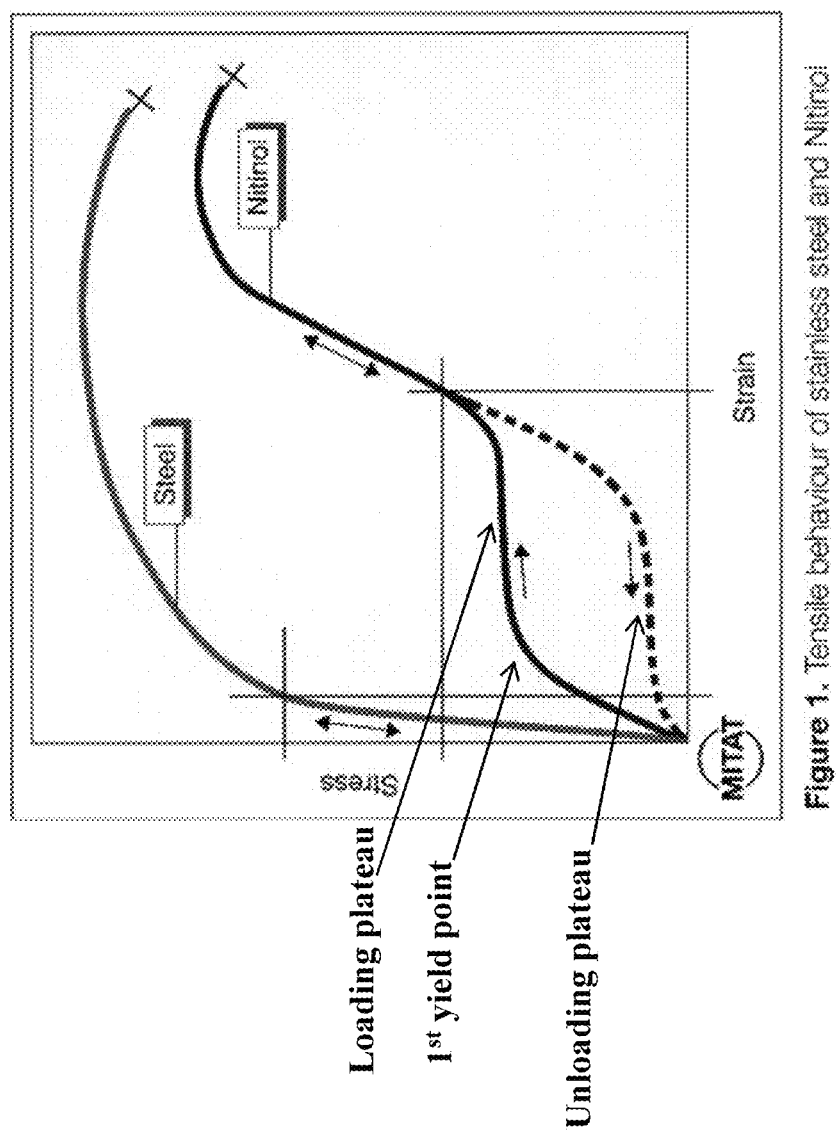
FIG. 12 shows the tensile behavior of stainless steel and Nitinol in accordance with one embodiment of the present invention.

Another illustrative advantage associated with a shape memory material spring in a spinal implant is its stress hysteresis. In most engineering materials, stress increases with strain in the elastic region when a load is applied to the material and decreases along the same path upon unloading. Some shape memory materials, such as Nitinol, exhibit a distinctly different behavior. FIG. 12 shows the tensile behavior of stainless steel and Nitinol. As shown in the Nitinol curve, stress first increases linearly with strain, up to 1% strain when a load is applied. After a first "yield point", several percentage points of strain can be accumulated with only a small amount of stress increase. The end of this plateau ("loading plateau") is reached at about 8% strain. After that, there is another linear increase of stress with strain. Unloading from the end of the plateau region causes the stress to decrease rapidly, until a lower plateau ("unloading plateau") is reached. Strain is recovered in this region with only a small decrease in stress. The last portion of the deforming strain is finally recovered in a linear fashion. The unloading stress can be as low as 25% of the loading stress. This looped stress/strain hysteresis is a shared phenomenon with bone, making the two materials compatible, as shown in FIG. 11.

A further illustrative advantage of using a shape memory material spring in a spinal implant is that its elasticity is temperature dependent. In other words, the plateau stresses are strongly temperature dependent above the transition temperature of the material. As a result, superelastic springs become stiffer when the temperature increases. The stiffness of a superelastic spring of a given design at a specific temperature (e.g., body temperature) can be modified to some extent by adjusting the transition temperature of the shape memory material. This adjustment can be done by heat treating the material. Lowering the transition temperature makes the spring stiffer at body temperature. Plotting the loading plateau stress (at a defined strain) versus the difference of body temperature and transition temperature yields a linear relationship with the stress increasing approximately 4.5 MPa per degree temperature difference for the most commonly used Nitinol alloys (e.g., alloy with a 50.8% titanium balance to nickel). In illustrative embodiments, the spring 12 has a tailored stiffness to optimize performance by either changing the material composition and/or the thermo-mechanical work applied to the material. To this end, a "sweet spot" of stiffness for torsional stability and matching bone modulus can be achieved by tuning the chemistry of the material and/or the work/heat treatment regime applied to the material.

Illustrative embodiments of the spinal implant 10 formed with a shape memory material spring can be manufactured in various different manners. In one example, after melting, a Nitinol ingot is forged and rolled into a bar or a slab at an elevated temperature. Nitinol billets and tubes are extruded at temperatures between 800° C. and 950° C. Such hot working processes break down the cast structure and improve mechanical properties. Next the billets are hot worked into the shape of the spring. An optimal hot working temperature is 800° C. At this temperature, the Nitinol alloy is easily workable and the surface oxidation is limited. Following hot working, the Nitinol spring is cold worked and may be heat-treated to obtain final dimensions with desired physical and mechanical properties.

In some cases, cold working of Nitinol is quite challenging because the alloy work-hardens rapidly and thus requires multiple reductions and frequent inter-pass annealing at 600-800° C. until the final dimension is obtained. In some illustrative embodiments, the spring 12 is formed from round wires. Round wires are produced by a die drawing process. Retaining surface oxide, Nitinol wires can be successfully drawn to small sizes.

Figure 13B:
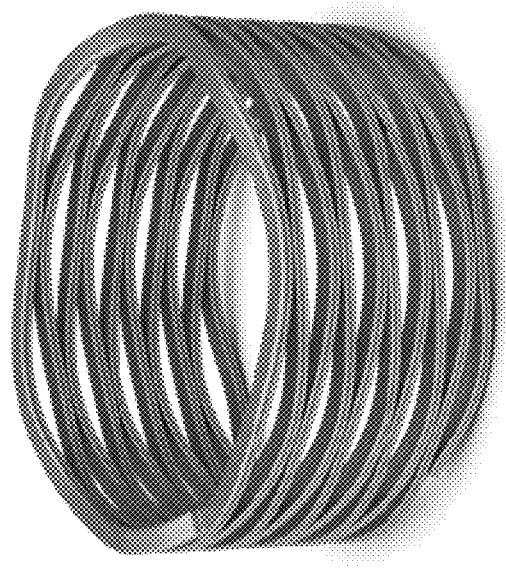
FIG. 13a shows one portion of a wave spring manufactured using flat wires and FIG. 13b shows a wave spring manufactured using flat wires in accordance with one embodiment of the present invention.
Figure 13A:
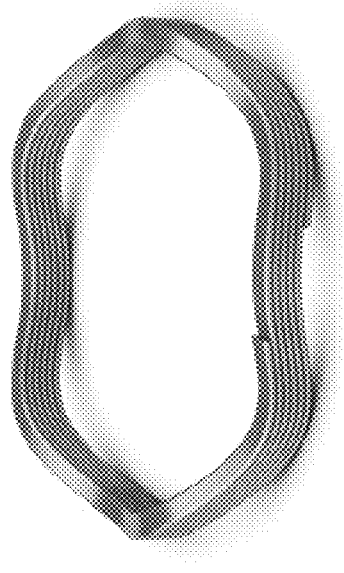

In other embodiments, the spring 12 is made from rectangular wires and/or flat wires. FIGS. 13a and 13b show a wave spring manufactured using flat wires in accordance with one embodiment of the present invention. Following a similar reduction schedule, rectangular wires can be manufactured by drawing round wires, while flat wires are typically produced by cold rolling. In accordance with illustrative embodiments of the present invention, as compared to rolled flat wires, the dimensions of drawn rectangular wires are much more tightly controllable. For example, typical tolerances for rolled wire are tighter than for drawn wires.

In some cases, a Nitinol spring is difficult to form at cold working temperatures because superelastic Nitinol exhibits significant spring-back when deformed in both cold worked and heat-treated states. Over-deformation of superelastic Nitinol induces martensite and therefore affects the mechanical and transformation properties. If the Nitinol spring is not constrained during heat treatment, the shape of the spring will recover partially back to its original configuration. Accordingly, illustrative embodiments of the Nitinol spring are fabricated by using a fixture to hold the spring in a fixed state during heat treatment. This process can be scaled up to production quantities by increasing the number of fixtures and heat treatment capacity. The formed spring is then placed and constrained in a fixture and subsequently heat treated to a desired shape with final properties. In illustrative embodiments of manufacturing a Nitinol wave spring, a flat wire is coiled very tightly at a temperature below the austenite start temperature and the wave spring is constrained during heat treatment.

In various illustrative embodiments of the present invention, to achieve optimized properties, materials with 30-40% retained cold work before heat treatment should be used. Superelastic Nitinol alloys are typically heat treated in the vicinity of 500° C. Lower temperatures in the range between 350° C. and 450° C. are also suitable for Nitinol alloys. Alternatively for Nitinol alloys with greater than 55.5% by weight nickel, good superelasticity and shape memory effect can be obtained by solution treatment at high temperatures between 600° C. and 900° C. and subsequent aging at a temperature around 400° C. This aging process induces precipitation hardening of nickel-rich phases. The transformation temperatures are elevated significantly as the matrix composition adjusts during aging.

Figure 14:
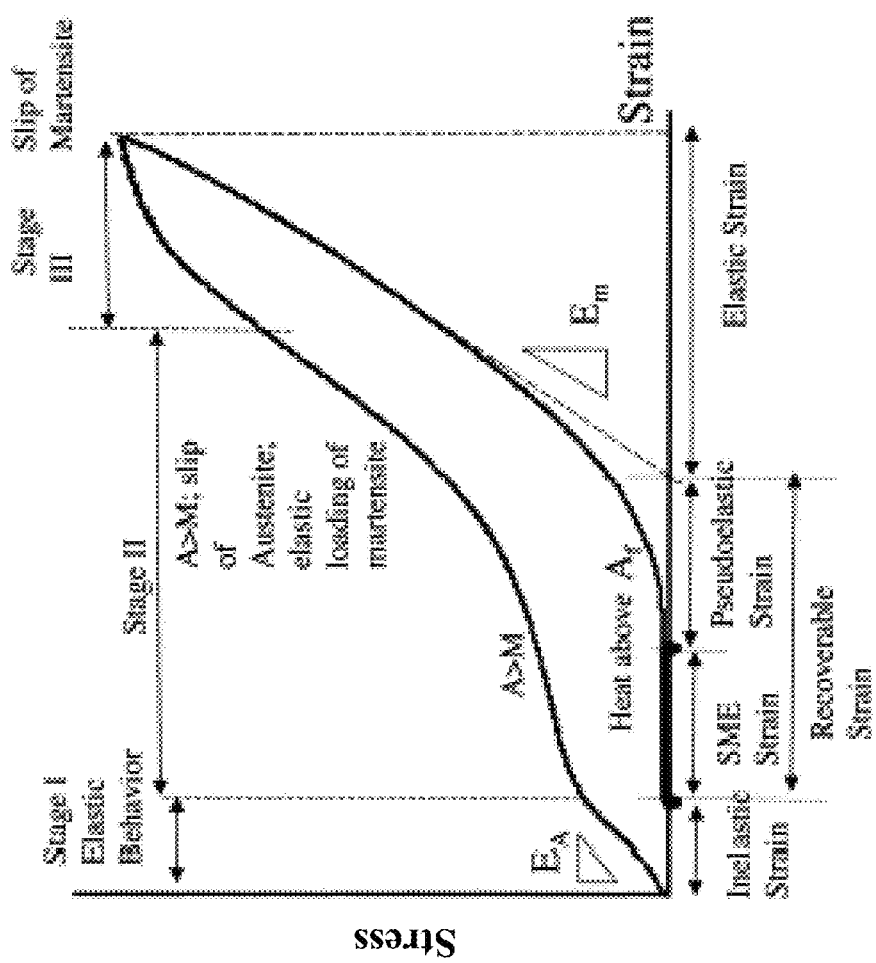
FIG. 14 shows a stress-strain curve for a superelastic shape memory material in accordance with one embodiment of the present invention.

Superelastic shape memory materials have the capability to fully regain the original shape from a deformed state when the mechanical load that causes the deformation is withdrawn. FIG. 14 shows a stress-strain curve for a superelastic shape memory material in accordance with one embodiment of the present invention. For some superelastic shape memory materials, the recoverable strains can be on the order of 10%. This phenomenon, termed as the pseudoelasticity or, superelasticity is dependent on the stress-induced martensitic transformation (SIMT), which in turn depends on the material's current temperature and the stress applied to the shape memory material. In one example, a shape memory material that is entirely in the parent (austenitic) phase is mechanically loaded (e.g., material's current temperature is greater than the material's austenitic start temperature). Thermodynamic considerations indicate that there is a critical stress at which the crystal phase transformation from austenite to martensite can be induced. Consequently, the martensite is formed because the applied stress substitutes for the thermodynamic driving force usually obtained by cooling the material. The mechanical load, therefore, imparts an overall deformation to the shape memory material specimen when a critical stress is exceeded. During unloading, because of the instability of the martensite at this temperature in the absence of stress, again at a critical stress, the reverse phase transformation starts from the stress-induced martensitic transformation to the parent phase. When the phase transformation is complete, the shape memory material returns to its parent austenite phase. Therefore, superelastic shape memory material shows a typical hysteresis loop (known as pseudoelasticity or superelasticity) and, if the strain during loading is fully recoverable, the loop becomes closed.

It should be noted that stress-induced martensitic transformation (or reverse stress-induced martensitic transformation) are marked by a reduction of the material's stiffness. Usually the austenite phase has a much higher Young's modulus in comparison with the martensite phase. In the case of a Nitinol wave spring, the more the spring is compressed, the more martensite is induced within the spring and, in turn, the spring becomes less stiff and more elastic. The advantage of this phenomenon is that, although the Nitinol spring provides more resistance as its being compressed, the spring also becomes more elastic and yielding because of the phase transformation from austenite to martensite. In this manner, the Nitinol spring acts as a better shock absorber for the spine. In contrast, steel springs do not exhibit this phenomenon and, when compressed to a certain point, the steel spring stiffens and could potentially apply an abrupt shock to the spine. Furthermore, the elasticity (or yieldability) of the spring can be tailored by modifying the material composition of the spring, modifying the work regime applied to the spring, modifying the heat treatment regime applied to the spring, and/or modifying the design of the spring (e.g., diameter, height, pitch of the spring, or the thickness of the wires).

A wave spring, e.g., made of Nitinol, can be designed to not only restore the height lost by a degenerative disc, but also to correct spinal deformities. As one ages, and one's intervertebral discs dehydrate, the spine can become arched, leading to a "hunched over" appearance. A wave spring, and preferably one made of Nitinol, can be formed in the shape of a wedge, e.g., be shape set to have a wedge shape (for easier insertion), and either by super elasticity or shape memory effect apply a restorative force to straighten the vertebral column.

Figure 15C:
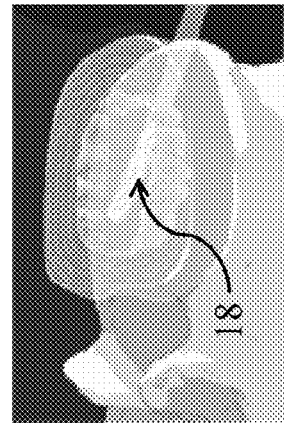
FIGS. 15A-15F shows a method for inserting a spinal implant in accordance with one embodiment of the present invention.
Figure 15F:
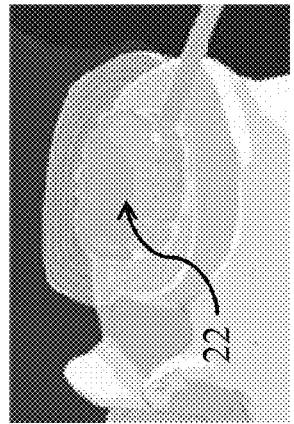
Figure 15B:
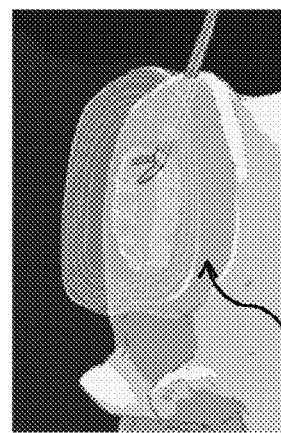
Figure 15E:
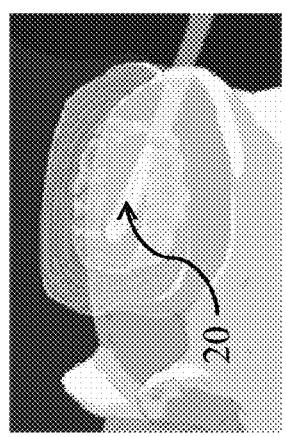
Figure 15A:
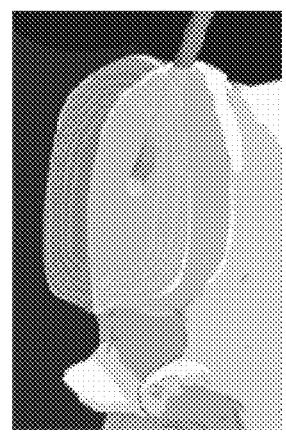
Figure 15D:
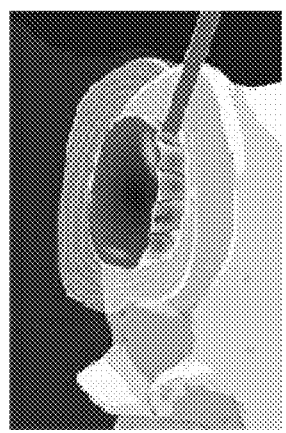

FIGS. 15A-15F show a method for inserting a spinal implant in accordance with one embodiment of the present invention. FIG. 15A shows a disc and nucleus removal procedure. After removal, FIG. 15B shows the insertion of a spring 12, such as a wave spring. Either before or after insertion of the spring, the entire nucleus may be removed. FIG. 15C shows a sizing/diagnostic balloon 18 being inserted into the disc space. FIG. 15D shows the balloon being filled with contrast solution. The contrast solution allows the balloon to be visible in a fluoroscopy. Images of the balloon can be taken in order to insure proper positioning and sizing of the balloon within the spring 12. The contrast material and catheter are then removed. FIG. 15E shows another catheter 20 with a balloon being inserted into the disc space. FIG. 15F shows a mixed polymer 22 passing through the catheter in liquid form and filling the balloon and the disc space. The polymer cures to form a firm but pliable inner disc, artificial nucleus 14, which is surrounded by the spring 12.

In accordance with illustrative embodiments of the present invention, a spinal implant 10 includes a wave spring 12 with a large cross sectional area. The spinal implant mimics the natural disc. The spinal implant 10 includes an inner artificial (polymer) nucleus area 14. Furthermore, in illustrative embodiments, the spinal implant includes contour endplates with teeth (not shown) that couple to the vertebrae.

Illustrative embodiments of the spinal implant 10 include a pliable modulus of elasticity which contributes to a broad and uniform distribution of pressure on the vertebral end plates. In various illustrative embodiments, the spinal implant 10 fills the entire volume of the disc cavity and contours the endplates, thus enhancing the load sharing between the annulus and the implant 10. Such a design facilitates stability and functional performance after implantation. In additional or alternative embodiments, the implantation of large volume spinal implant through a small annulotomy prevents migration of the implant. Furthermore, illustrative embodiments of the present invention contribute to prevent endplate reaction with the bone surface and thereby prevent loosening, in contrast to other disc and nucleus replacement devices reported clinically.

In some embodiments, the spiral implant may include a polymer sheath (not shown) surrounding the spring 12 and the nucleus 14 in order to prevent bone in-growth.

The embodiments of the invention described above are intended to be merely exemplary; numerous variations and modifications will be apparent to those skilled in the art. All such variations and modifications are intended to be within the scope of the present invention.

What is claimed is:

1. A spinal implant comprising:
   a coiled wave spring configured to surround a nucleus, wherein the wave spring is formed with at least one wire having a sinusoidal shape and made of a shape memory material, wherein the shape memory material is tailored to achieve a stress-induced martensitic transformation when a critical stress is exceeded and the shape memory material is further trained to expand to a preset shape when the wave spring temperature exceeds its transition temperature.

2. The spinal implant according to claim 1, wherein the wave spring is wedge shaped.

3. The spinal implant according to claim 1, wherein the shape memory material is selected from the group consisting of Nitinol, a Titanium-Niobium alloy, and combinations thereof.

4. The spinal implant according to claim 1, wherein the wave spring is formed with one or more flat wires.

5. The spinal implant according to claim 1, wherein the wave spring is formed with one or more rectangular wires.

6. The spinal implant according to claim 1, further comprising:
   an artificial nucleus configured to simulate a disc nucleus, wherein the wave spring surrounds the artificial nucleus.

7. The spinal implant according to claim 6, wherein the artificial nucleus is made from a polymer material.

8. The spinal implant according to claim 6, wherein the artificial nucleus is made from a hydro-gel material.

9. The spinal implant according to claim 6, wherein the artificial nucleus is a wave spring.

10. A method of forming a spinal implant, the method comprising:
    forming a coiled wave spring, the wave spring having at least one wire with a sinusoidal shape and made of a shape memory material, wherein the shape memory material is tailored to achieve a stress-induced martensitic transformation when a critical stress is exceeded and the shape memory material is further trained to expand to a preset shape when the wave spring temperature exceeds its transition temperature; and
    configuring the wave spring to surrounding a nucleus.

11. The method according to claim 10, wherein the wave spring is wedge shaped.

12. The method according to claim 10, wherein the shape memory material is selected from the group consisting of Nitinol, a Titanium-Niobium alloy, and combinations thereof.

13. The method according to claim 10, wherein the wave spring is formed with one or more flat wires.

14. The method according to claim 10, wherein the wave spring is formed with one or more rectangular wires.

15. The method according to claim 10, further comprising forming an artificial nucleus configured to simulate a disc nucleus, wherein the wave spring surrounds the artificial nucleus.

16. The method according to claim 15, wherein the artificial nucleus is formed from a polymer material.

17. The method according to claim 15, wherein the artificial nucleus is formed from a hydro-gel material.

18. The method according to claim 15, wherein the artificial nucleus is formed from a wave spring.

19. A method of implanting a spinal implant, the method comprising:
    inserting a coiled wave spring into an intervertebral space, wherein the wave spring is formed with at least one wire having a sinusoidal shape and made of a shape memory material, wherein the shape memory material is tailored to achieve a stress-induced martensitic transformation when a critical stress is exceeded and the shape memory material is further trained to expand to a preset shape when the wave spring temperature exceeds its transition temperature; and
    introducing a nucleus material into an interior area of the wave spring, the nucleus material configured to simulate a disc nucleus.

20. A method of forming a spinal implant, the method comprising:
    providing a shape memory material with about 30-40% cold work;
    coiling a wave spring, the wave spring having at least one wire with a sinusoidal shape and made of the shape memory material, wherein the shape memory material is tailored to achieve a stress-induced martensitic transformation when a critical stress is exceeded; and
    subsequently age heat treating the shape memory material after coiling the wave spring.

* * * * *